(12) United States Patent
Couderc et al.

(10) Patent No.: US 10,555,702 B1
(45) Date of Patent: Feb. 11, 2020

(54) METHODS AND SYSTEMS FOR CHARACTERIZING THE QUALITY OF AN ELECTROCARDIOGRAM SIGNAL

(71) Applicant: eResearchTechnology, Inc., Philadelphia, PA (US)

(72) Inventors: Jean-Philippe Y. Couderc, Rochester, NY (US); Thuan G. Pham, Rochester, NY (US); Alexander Zapesochny, Rochester, NY (US)

(73) Assignee: eResearchTechnology, Inc., Philadelphia, PA (US)

( * ) Notice: Subject to any disclaimer, the term of this patent is extended or adjusted under 35 U.S.C. 154(b) by 166 days.

(21) Appl. No.: 15/583,723

(22) Filed: May 1, 2017

(51) Int. Cl.
  *A61B 5/04* (2006.01)
  *A61B 5/00* (2006.01)
  *A61B 5/0456* (2006.01)
  *G06F 5/01* (2006.01)
  *G16H 50/30* (2018.01)
  *G16H 10/20* (2018.01)
  *G16H 50/20* (2018.01)

(52) U.S. Cl.
  CPC ........ *A61B 5/7221* (2013.01); *A61B 5/04012* (2013.01); *A61B 5/0456* (2013.01); *A61B 5/7203* (2013.01); *G06F 5/01* (2013.01); *G16H 10/20* (2018.01); *G16H 50/20* (2018.01); *G16H 50/30* (2018.01)

(58) Field of Classification Search
  CPC ... A61B 5/7221; A61B 5/7203; A61B 5/0456; A61B 5/04012; G06F 5/01; G16H 50/30; G16H 10/20; G16H 50/20

USPC .......................................................... 600/521
See application file for complete search history.

(56) References Cited

U.S. PATENT DOCUMENTS

| | | | |
|---|---|---|---|
| 5,560,368 A * | 10/1996 | Berger | A61B 5/0472 600/516 |
| 6,370,423 B1 * | 4/2002 | Guerrero | A61B 5/044 600/513 |
| 10,025,910 B2 | 7/2018 | Paty et al. | |
| 10,049,368 B2 | 8/2018 | Hansen et al. | |
| 2007/0055481 A1 | 3/2007 | Baird et al. | |
| 2016/0045117 A1 * | 2/2016 | Liu | A61B 5/7221 600/485 |

OTHER PUBLICATIONS

Co-pending U.S. Appl. No. 15/604,368, filed May 24, 2017.

(Continued)

*Primary Examiner* — Amanda K Hulbert
*Assistant Examiner* — Natasha Patel
(74) *Attorney, Agent, or Firm* — Wilson, Sonsini, Goodrich & Rosati, PC

(57) ABSTRACT

Described here are methods, devices and systems for characterizing a physiological signal such as an electrocardiogram (ECG) signal. Generally, the method includes receiving the ECG signal generated by an ECG device coupled to a patient. ECG signal quality for a plurality of consecutive beats may be determined based on a dispersion coefficient and a deviation from an average of each of a plurality of ECG parameters. Indexing information may be generated for set of sequences from the plurality of consecutive cardiac beats. Each of the sequences may comprise a first predetermined number of consecutive cardiac beats. The set of the sequences may be ordered based upon the ECG signal quality.

18 Claims, 6 Drawing Sheets

(56) References Cited

OTHER PUBLICATIONS

Co-pending U.S. Appl. No. 16/007,633, filed Jun. 13, 2018.
Co-pending U.S. Appl. No. 16/020,109, filed Jun. 27, 2018.
U.S. Appl. No. 15/291,103 Office Action dated Oct. 5, 2018.
U.S. Appl. No. 15/955,461 Office Action dated Aug. 9, 2018.

* cited by examiner

METHODS AND SYSTEMS FOR CHARACTERIZING THE QUALITY OF AN ELECTROCARDIOGRAM SIGNAL

FIELD

Devices, systems, and methods herein relate to ranking quality of a physiological signal, specifically an electrocardiogram (ECG) signal.

BACKGROUND

Documented cases of fatal and non-fatal torsade de pointes (TdP), a type of lethal ventricular arrhythmia, associated with the use of new chemical entities (NCE) have resulted in the withdrawal of a number of drugs from the market. In further response to these public health concerns, the International Council for Harmonization Guidance (ICH E14) has been implemented to guide drug developers in the conduct of thorough cardiac safety assessments on all NCEs and has since virtually eliminated post-market drug withdrawals due to arrhythmia and sudden cardiac deaths. Beginning from 2005, nearly all new compounds in development have been expected to undergo rigorous testing for their potential to prolong the QT interval (a surrogate marker of proarrhythmia) on an electrocardiogram (ECG).

New drugs seeking regulatory approval typically undergo systematic evaluation of the potential to cause QT prolongation in a Thorough QT (TQT) study in healthy subjects or as part of an intensive assessment of ECGs collected from Phase I trials using exposure response modeling. Prior to characterizing a drug's QT liability in a TQT or Phase I study, subjects with a marked baseline prolongation of QT/QTc interval are generally excluded from participating in a clinical study. For example, subjects with a measured QTc interval in excess of 450 milliseconds during screening for a late-phase study are often excluded from the trial. Underlying QT prolongation has been shown to be associated with a broad range of disease states, including liver disease, oncology, diabetes, rheumatoid arthritis and some central nervous system conditions. The share of subjects who have measured QT prolongation has been shown in studies to be higher than in the population of healthy subjects as a whole. Research studies have also shown that QT prolongation may also be more prevalent in individuals that are older or obese, or that are experiencing depression, anxiety or sleeplessness, which are all conditions or characteristics that may commonly be encountered in clinical trial subjects.

Furthermore, site-based ECG machines and the automated QTc readings they produce are often relied upon to measure the QT/QTc interval for the purpose of making subject inclusion/exclusion decisions, and studies indicate that these automated machine measurements often produce QT measurements that substantively diverge from, and which are often longer than, QT measurements made at centralized ECG core laboratories, resulting in unnecessary patient exclusions and lower patient recruitment yields. Consequently, automated QT/QTc measurements derived from many ECG devices are not accurate or precise enough to optimize correct subject inclusion/exclusion decision making, especially when subjects have an underlying QT/QTc that is close to the exclusion threshold or when ECGs exhibit unusual morphologies. To compensate for these inefficiencies, more subjects are recruited, thus raising costs and the time required to complete a study.

Additionally, even when QT/QTc measurements are made at a centralized ECG core laboratory rather than being derived automatically from ECG devices at a clinical trial site, a significant amount of variability in these measurements may occur based on the quality and variability of the cardiac beats that are selected for measurement. Selecting poor quality cardiac beats, or cardiac beats that contain outlier values compared to most of the other cardiac beats for that subject at that time, may include QT/QTc measurements that do not accurately represent the state of the subject. This can lead to potential issues in any clinical study where QT/QTc is being measured. For example, skewed QT/QTc values generated from mixed quality ECG tracings may unnecessarily exclude otherwise eligible patients and/or incorrectly include ineligible patients that can impact study outcomes. This may result in incorrect conclusions about adverse events or about a drug's overall effect on the QT interval. Finally, drug developers often must report not only QT/QTc measures but also on their drug's effect on PR and QRS intervals, which are other measurements derived from an ECG. Selecting high quality cardiac beats enables more accurate and precise measurements of PR and QRS values. Accordingly, it would be desirable to characterize the quality of an electrocardiogram signal for determining QT liability, as well as for making correct conclusions about a subject's QT, PR, and QRS intervals, and other ECG characteristics.

BRIEF SUMMARY

Described here are devices and methods for characterizing the quality of an ECG signal. In general, methods for characterizing an ECG signal may comprise receiving an ECG signal or completed recording generated by an ECG device coupled to a patient or subject. The entire ECG recording, or a selected epoch from the entire ECG may be used for the analysis. The duration of an epoch may be specified by the protocol or industry standards, and is typically around a 5-minute ECG recording segment, or longer, and representative of a timepoint of that patient in a clinical study (e.g., control phase, washout phase, post-treatment time point, etc.) Individual cardiac beats and smaller consecutive sets or segments of beats may be analyzed based on a dispersion coefficient and a deviation from the average of each of a plurality of ECG parameters. In some examples, a specified group or number of consecutive beats (e.g., a multi-beat sequence of three consecutive beats), may be analyzed sequentially or in an overlapping fashion, using a dispersion coefficient and deviation of the sequence within the full ECG tracing, to identify longer segments of similar consecutive beats. These sequences or replicates may be specified with a fixed duration or beats (e.g., in the range of three to ten beats) or a minimum duration or number of beats (e.g., 10 seconds or longer) and would include one or more of sequential or overlapping multi-beat sequences. In a stable, high quality ECG recording, the replicate may comprise the entire epoch or full ECG. The identifier information and/or associated ECG parameters may be used to visually or digitally annotate the full ECG tracing, or may be used by a viewing program to select sequences within full or raw ECG tracing for display and analysis by a reviewer or technician. A relative ranking of the sequences based upon the sequence length, dispersion, and/or deviation may be provided, which may facilitate efficient review. The determined set of ECG signal quality values may represent a set of adaptive quality scores that are indicative of the set of sequences and/or epochs best suited for further QT evaluation.

In some variations, the ECG signal or recording comprises an epoch and a set of replicates, where each replicate in the epoch containing a predetermined number of consecutive cardiac beats or pre-determined period of time. The ECG signal quality may be determined for each replicate. In some variations, a method of characterizing an ECG signal may include receiving an ECG signal generated by an ECG device coupled to a subject. ECG signal quality of a plurality of consecutive cardiac beats may be determined based on a dispersion coefficient and a deviation from an average of each of a plurality of ECG parameters. Indexing information may be generated for a set of sequences from the plurality of consecutive cardiac beats. Each of the sequences may comprise a first predetermined number of consecutive cardiac beats. The set of the sequences may be ordered based upon the ECG signal quality.

In some variations, the ECG signal may comprise an epoch comprising a second predetermined number of consecutive cardiac beats. The ECG signal quality may be determined for each sequence of the set of sequences. The deviation from average may comprise a sum of differences between the interval and an average of the epoch for each of the plurality of ECG parameters. The ECG signal quality may be given by the equation Q=DP*($\Sigma \bar{x}$), where DP is the dispersion coefficient and $\bar{x}$ is the deviation between the interval and the average of the epoch for the ECG parameter. The dispersion coefficient may be based on a range and a normalized range of the interval for each of the plurality of ECG parameters. The dispersion coefficient may be an evenly weighted sum of the normalized range of the plurality of ECG parameters. The range may be given by the equation Rep(x)=Max(x)−Min(x), where x comprises one of the ECG parameters. The normalized range may be given by the equation $$\overline{\hat{Rep}}(x) = \frac{Rep(x)}{\bar{x}},$$

where $\bar{x}$ is an average value of one of the ECG parameters within the epoch.

The method may include additional variations. The ECG parameters may comprise QT, PR, and QRS intervals, for example. The first predetermined number may be two or more, but in other examples may be in the range of n to m beats, such as 3 to 100 beats, 3 to 50 beats, 5 to 20 beats, or 3 to 10 beats, for example. A number of ECG signal quality values of the epoch may equal n number of cardiac beats minus two if all the cardiac beats are sinus beats. The second predetermined number may be greater than the first predetermined number. The set of sequences associated with the PQRST complexes may be ordered in ascending order based on the ECG signal quality, with lower values indicating higher quality. A subset of the ordered intervals may be selected for QT evaluation associated with a new chemical entity using the index information. The QT evaluation may comprise one or more of a Thorough QT (TQT) study, phase I study, phase II study and/or phase III study. Subject determination in one or more studies may be determined using the index information. In some of these variations, subject participation comprises exclusion from the one or more studies when the QT evaluation comprises a QTc in excess of 450 milliseconds. A subset of the ordered sequences may be selected for one or more of QRS and PR evaluation associated with a new chemical entity using the index information.

In some variations, the ECG device may be connected to the subject, ECG signal quality of the plurality of consecutive cardiac beats may be determined prior to disconnecting the ECG device from the subject, and the ECG device may be disconnected from the subject. In some of these variations, a second ECG signal may be received from the ECG device coupled to the subject if the ECG signal quality of the plurality of consecutive cardiac beats exceeds a predetermined threshold corresponding to one or more of the dispersion coefficient and the deviation from the average of each of the plurality of ECG parameters.

Also described here are devices for characterizing an electrocardiogram (ECG) signal. In general, these devices comprise a receiver configured to receive an ECG signal generated by an ECG device coupled to a subject. The ECG signal may comprise a plurality of consecutive cardiac beats. A controller may comprise a processor and a memory. The controller may be configured to determine ECG signal quality of the plurality of consecutive cardiac beats based on a dispersion coefficient and a deviation from an average of each of a plurality of ECG parameters. The controller may generate indexing information for a set of sequences from the plurality of consecutive cardiac beats. Each of the sequences may comprise a first predetermined number of consecutive cardiac beats. The set of the sequences ordered based upon the ECG signal quality.

DETAILED DESCRIPTION

Figure 1:
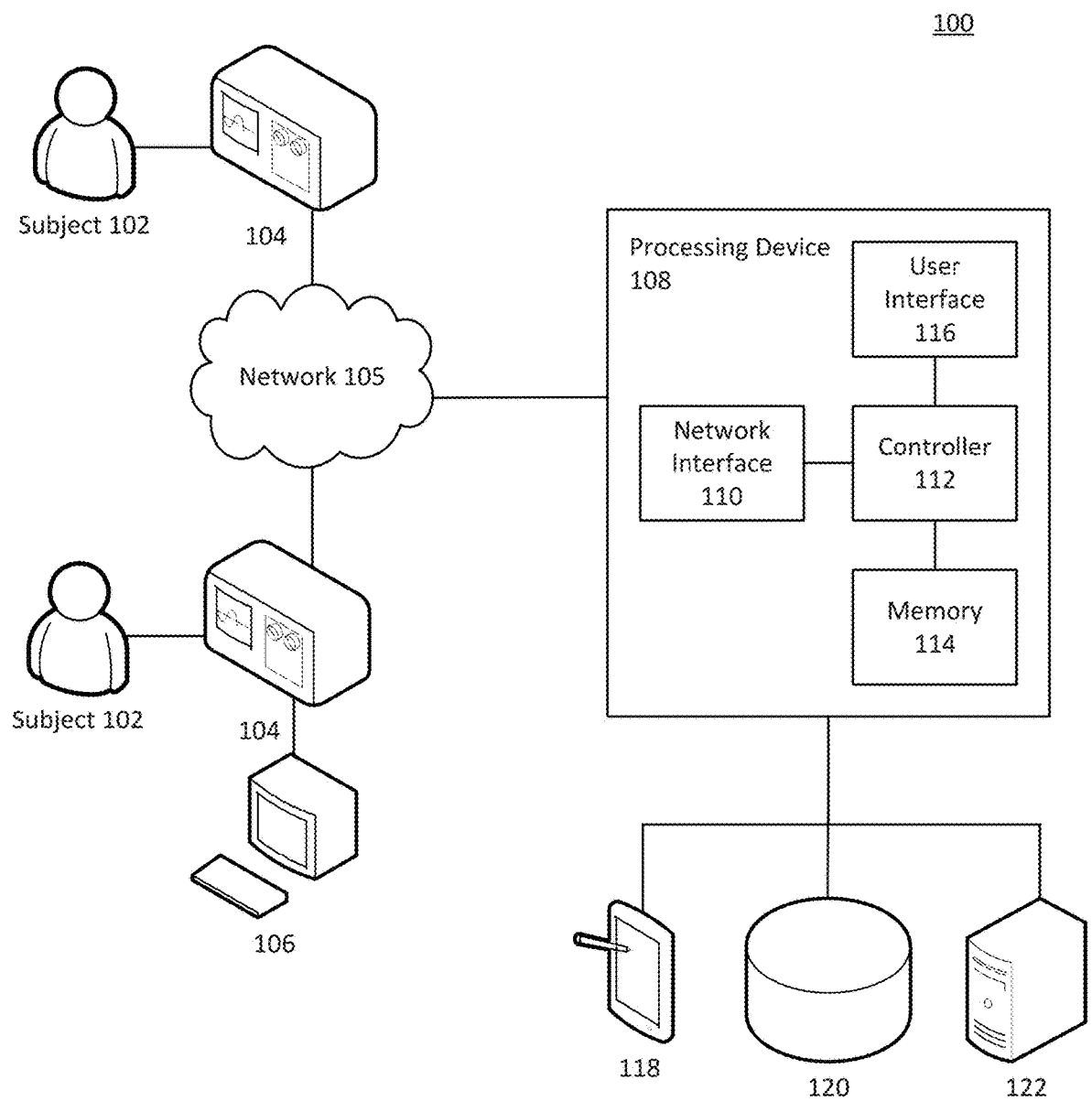
FIG. 1 depicts one variation of a system comprising an ECG device coupled to a patient.

Generally described here are devices, systems, and methods for analyzing a physiological signal to rank at least one subject parameter. More particularly, described herein are devices, systems, and methods for characterizing ECG signal quality. In some variations, the devices, systems, and methods described herein may generate index information comprising an ordered set of cardiac beat sequences best suited for QT evaluation and analysis. The sequences may include the time durations of specific morphologies within a PQRST complex, such the PR, QT and QRS intervals, or the time durations between two adjacent PQRST complexes, such as the RR interval. In some variations, the devices, systems, and methods described herein may provide a set of sequences that may be used to determine a subject's participation in one or more clinical trials, from early to late stage studies.

Determination of ECG characteristics on a full set of raw ECG recordings generated by clinical trial studies may sometimes be unreliable as noise and a patient's physiological variability during ECG recording may result in inaccurate ECG interval measurements, which in some cases could lead to a subject's unnecessary exclusion from, or inappropriate inclusion in, an ECG study. For example, some clinical trial subjects may be inappropriately excluded from participation if analysis of their ECG indicates that they are above a static threshold criteria (e.g., QTc≥450 ms).

Importantly, consistent and reliable QT evaluation has been previously difficult in early stage clinical trials due to a lack of accuracy and precision. The devices, systems and methods described herein may be applied across a wide range of clinical trials, from early to late stage studies in order to gain early or more detailed insight into the cardiac safety profile of a drug. A significant proportion of traditional TQT studies have found that a therapeutic candidate or other biologically active agent to be potentially arrhythmia inducing. However, by accurately determining a cardiac safety profile in an early stage clinical trial, resources may be shifted away from high risk drugs before even more significant investment and development efforts are undertaken. Increased efficiency may also be realized if reliable cardiac safety data is generated from early stage studies that are routinely performed as part of the clinical development program. Thus, the early acquisition of reliable cardiac safety data significantly benefits the risk management of a drug development program.

Ranking a set of multi-beat sequences (MBS) (e.g., a sequence of three consecutive cardiac beats) may be based on variability of a multi-beat sequence relative to other multi-beat sequences in the epoch. Variability may be due to deviations caused by noise and other factors and may be identified based on signal differences between intervals in the epoch. A ranking of the set of MBS allows the least variable beats having the highest quality to have higher priority and the most variable beats having the lowest quality to have lower priority, and therefore be less likely to be selected for QT evaluation. By selecting the MBS determined as higher quality, QTc and other parameters derived in clinical studies (e.g. QRS and PR) may be more accurately analyzed, which may in turn improve clinical study decision making, such as a NCE's effect on ECG segments and/or a subject's participation in a clinical study.

Additionally, QT evaluation based on ranked ECG signal quality as described herein may be more accurate and precise, thus increasing confidence in subject recruitment decisions for a clinical trial. For instance, unnecessary patient exclusion related to falsely-elevated, imprecise ECG machine interpreted QT intervals may be minimized through analysis of high quality ECG signal segments. For example, once QT liability has been accurately characterized as described in more detail below, it may be determined that subjects with a measured QTc, as determined by an automated reading at a site-based ECG machine, in excess of 450 milliseconds does not actually need to be excluded from a study. As a result, recruitment may be accelerated, resulting in an earlier database lock, leading to significant cost savings during phase II and III studies, for example.

In some variations, proarrhythmia risk may be assessed in First-in-Human (FIH) studies, such as single ascending dose (SAD) or multiple ascending dose (MAD) studies. The minimum number of subjects per cohort/dose groups in a FIH study may be six to nine subjects. Even though doses are distributed across several small cohorts, an intense ECG assessment schedule where such ECGs are assessed in a reliable and precise manner, and where such ECG data is subsequently analyzed using a statistical technique such as exposure response modeling, may provide cardiac safety data with at least the same level of confidence as a TQT study.

Accordingly, the cardiac risk assessment traditionally obtained in a TQT study may be achieved through robust ECG monitoring and exposure-response (ER) analysis of data generated from SAD and/or MAD studies. The cardiac safety assessment conducted in conjunction with an FIH study may be provided at a fraction of the cost of a TQT study that typically requires millions of dollars and a significant timeframe to plan and execute. In addition, earlier reliable assessment of cardiac safety data may altogether replace a late stage, resource intensive TQT study. This may significantly decrease the overall development cost and/or time to bring a new drug to market.

Figure 4:
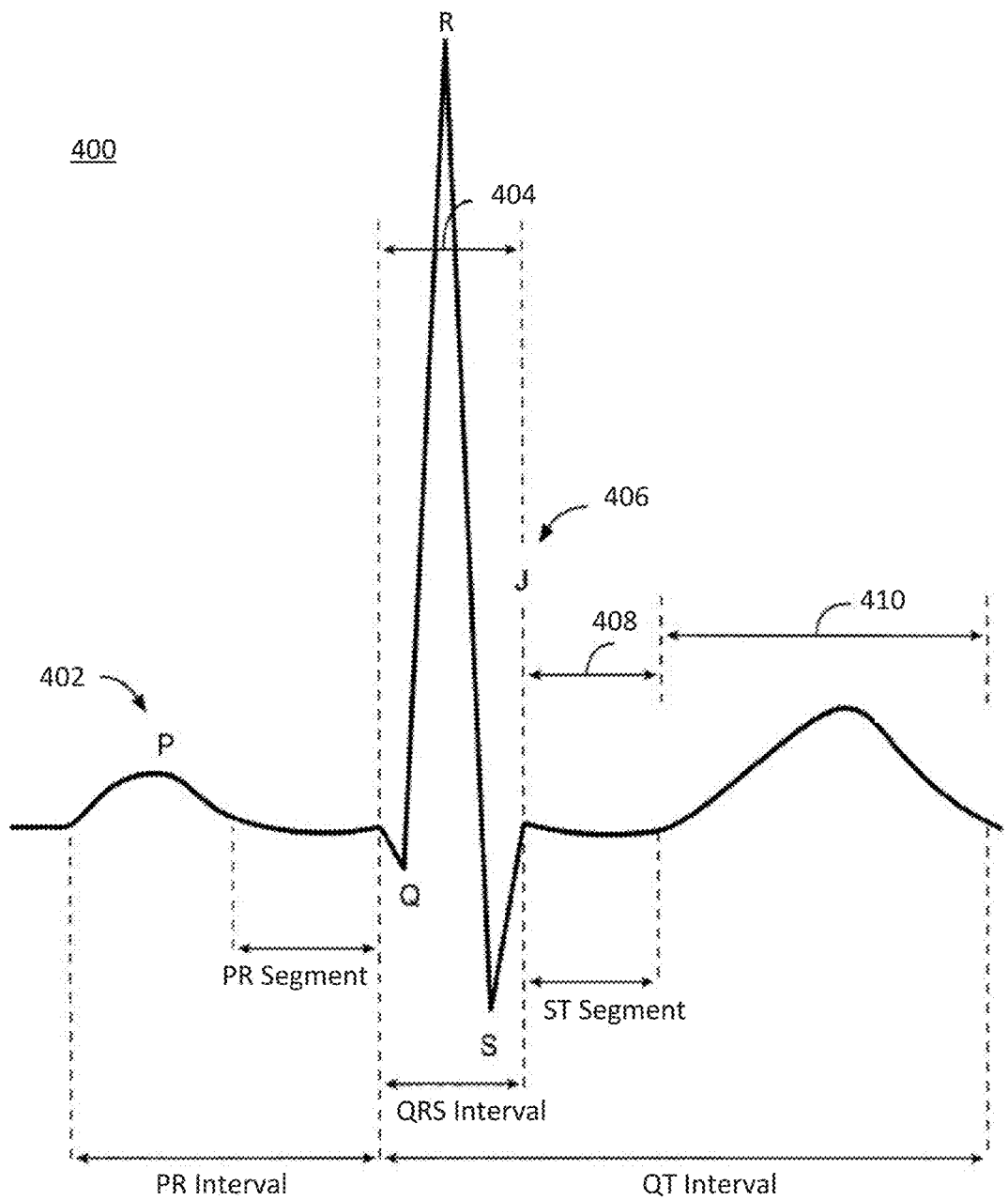
FIG. 4 is an illustrative ECG waveform of cardiac electrical activity.

FIG. 4 illustrates an exemplary ECG waveform (400) of normal cardiac electrical activity generated by an electrocardiograph device plotted as a function of voltage and time. Initially, a P-wave (402) caused by atrial depolarization is observed having a relatively short duration rounded positive deflection. Subsequent to this, the Q-wave provides a small but sharp negative deflection. Next, an R-wave includes a very large and sharp positive deflection, after which an S-wave provides a sharp and large negative deflection. The presence of these deflections is not systematic and according to the angle of the recording QRS complex can have more simple configuration such as QR, or RS amongst others.

When the Q, R, and S waves are taken together, they are known as the QRS complex (404). The QRS complex (404) is caused by ventricular depolarization. The PR interval is measured from the beginning of the P-wave (402) to the beginning of the QRS complex. The QRS complex (404) ends at J-point (406). The J-point (406) is also the point at which the ST segment (408) begins, the ST segment (408) being associated with the period when the ventricles are depolarized. The ST segment (408) is followed by a T-wave (410) that provides a relatively long duration rounded positive deflection and represents the repolarization of the ventricles. The JT peak interval is from the J point to the apex of the T-wave and represents a sub-interval of the QT interval. The QT interval is measured from the beginning of the QRS complex (404) to the end of the T-wave (410). Abnormalities in the QT interval (including the JT peak interval) often mark susceptibility to life-threatening arrhythmias as discussed above.

ECG parameters such as the QT interval, QRS complex (e.g., QRS onset, QRS offset), J point, T-wave (e.g., T-wave apex, T-wave endpoint), and other features may be determined from ECG signal data in a variety of ways. The devices, systems, and methods described herein may comprise one or more of the methods for detecting ECG parameters described in U.S. Pat. No. 7,463,921, filed on Aug. 13, 2002, and titled "METHOD AND SYSTEM FOR ANALYZING AN ELECTROCARDIOGRAPHIC SIGNAL," and/or U.S. Pat. No. 7,912,535, filed on Mar. 1, 2007, and titled "METHOD AND SYSTEM FOR ASSESSING RPOLARIZATION ABNORMALITIES," each of which is hereby incorporated by reference in its entirety. In some variations, a corrected QT interval may be calculated by using one or more Bazett, Fridericia, and Framingham corrections, given below:

Bazett $QTc=QT*RR^{1/2}$

Fridericia $QTcF=QT*RR^{1/3}$

Framingham $QTc=QT+0.154+0.154*(1000-RR)$

In other variations, an ECG signal quality processing device may be provided remotely relative to an ECG device connected to a subject. In this manner, clinical ECG devices may be utilized to record subject data without relying on the poor accuracy of their internal QT reading algorithms. This allows for faster and more consistent ECG analysis across different studies and locations.

I. Systems

Devices for characterizing an ECG signal generally include a receiver for receiving ECG signal data and a processor and memory for analyzing the received data to determine ECG signal data quality. The receiver may be configured to receive the ECG signal generated by an ECG device coupled to a patient. The processor may be configured to determine ECG signal quality for each of a plurality of ECG parameters. In some variations, ECG signal quality is determined based on a dispersion coefficient and a deviation from average of each of a plurality of ECG parameters. In some variations, the device may be provided remotely from the ECG device and the patient and communicate over a network. The processor may be further configured to provide the ECG signal quality for QT evaluation associated with a new chemical entity.

Overview

FIG. 1 depicts one variation of a system (100) comprising a subject (102) coupled to an ECG device (104) at a patient or clinical study site. The patient site may further include an on-site computing device (106) configured to communicate with the processing device (108) and provide information to a user such as a subject (102), reviewer, ECG technician, and the like. The subject (102) may be connected to the ECG device (104) through a set of leads and generate ECG signal data received by the processing device (108) over a network (105) such as a wireline or wireless network. An output of the device (108) may be transmitted to one or more of the ECG device (104), computing device (106) and other computing devices (118, 120, 122) (e.g., database, server, and the like). Data transmission may be provided through Hyper Text Transfer Protocol Secure (HTTPS) or other data transmission protocol. Data may be encrypted on any of the devices described herein.

In some variations, an ECG signal generated at the ECG device (104) may be transmitted to a centralized ECG laboratory including processing device (108) for processing and analysis, thus avoiding signal analysis performed by the ECG device (104) using its internal automated measurement algorithms, which may generate incorrect results or falsely elevated QTc readings. This is significant as some studies show that the prevalence of incorrectly elevated QTc readings using common ECG devices and their automated measurements as compared to measurements performed at a centralized ECG laboratory. For example, some studies indicate that up to 30% of subjects using the automated ECG device derived readings indicate that their QTc intervals are above key exclusion thresholds (>450 ms, >470 ms, >500 ms) when their QTc readings may be below those thresholds when their ECGs are processed using the methods described herein. For example, centralized processing may improve study recruitment through more consistent and reliable analysis of ECG signal data. In some variations, the processing device (108) may be provided on-site with the subject (102), incorporated into an ECG device (104), and/or the computing device (106).

ECG Device

As discussed above, an ECG device (104) may be provided for ECG data collection and patient safety but need not be used to determine a final QT measurement. The ECG device (104) may record ECG signal data from a subject using a set of ECG leads coupled to the subject (102) at the ECG device (104). An appropriate number of ECG leads (not shown), positioned at an appropriate subject body site, may be used. ECG data may be recorded from a plurality of lead locations on a subject body surface. Examples of ECG lead systems include a standard 12-lead electrocardiogram (e.g., leads I, II, III, aVR, aVL, aVF, V1, V2, V3, V4, V5 and V6), Mason-Likar (upper body limb lead placement), and "Frank" electrode lead system (e.g., 7 electrodes). Other examples include the addition of right-sided precordial leads, posterior leads, leads placed in higher or lower intercostal spaces, and the like.

The ECG signal data generated by ECG device (104) may be generated in any of the known digital ECG formats. In some variations, ECG signal formats may include, but are not limited to, the Standard Communications Protocol for computer assisted ElectroCardiography (SCP-ECG), HL7 annotated ECG (HL7 aECG), Digital Imaging and Communication in Medicine (DICOM) Waveform Supplement 30 and Medical waveform Format Encording Rules (MFER). Any known digital ECG format may be utilized in conjunction with the devices and methods described herein.

In some variations, continuous ECG digital signal data recordings with high-resolution (e.g., 1000 Hz, 16-bit resolution or 500 Hz sampling rate and 12-bit amplitude resolution) acquired from a subject are received by the processing device (108). The ECG signal data may include a plurality of cardiac beats and corresponding time point (TP), an optional section of the ECG of a pre-specific length by time duration or number of beats (which may provide consistency of recording length), information which are relative time stamps at which drug concentration or other information relevant to the aim of a clinical study are measured.

ECG data signals generated by the ECG device (104) may be affected by noise from one or more different sources, including physiological and non-physiological sources. Examples of physiological noise include axis shift, biphasic QRS morphology and QRS amplitude variations. Non-physiological noise sources may include 50/60 Hz electric power lines, electrode motion artifacts and baseline wander. Noise in an ECG signal may cause two types of beat detection errors: A false positive (FP) occurs when a beat detection algorithm falsely generates a sense marker (i.e., an indication of a beat) when there is no QRS complex; a false negative (FN) occurs when a beat detection algorithm fails to detect the true QRS complex. The ECG device (104) may transmit one or more of the raw ECG signal data and/or filtered signal data having signal noise removed. The ECG device (104) may be coupled to one or more devices (e.g., on-site device (106), processing device (108), and the like) and/or networks (105) to communicate.

Processing Device

A controller (112) may be configured to perform processing of ECG data, such as determining ECG signal quality and generating index information corresponding to a ranking of multi-beat sequences of the ECG signal. For example, the processing device (108) processes the ECG signal data to generate a set of ordered beats based on quality. In one variation, the device (108) may receive ECG data from a plurality of ECG devices (104) through network (105). Accordingly, the device (108) may provide centralized data collection and standardized ECG signal processing across a plurality of study locations, subjects and throughout a timeline of a study. The device (108) may also allow an authorized user to easily access and review patient study results and perform additional analysis. For instance, different levels of patient results may be available to one or more sponsors and authorized internal and/or external users via a web-based interface. As another example, end-of-study reporting may be required by sponsors and/or some domestic or international regulatory agencies. Record keeping, security and consistency may thus be improved when data processing and data storage is centralized at a processing device (108). This also allows trained personnel such as cardiologists that manually process and review ECG data to be provided access at a central location, further increasing efficiency and cost savings.

The user interface (116) may comprise an input device and output device, including a display providing a user, such as a cardiologist, a set of evaluable beats for analysis. FIG. 3 depicts one variation of a graphical user interface (GUI) (300) of an ECG device (104). In FIG. 3, a set of nine beats are displayed together on GUI (300) per time point. For instance, the three best beats (304, 306, 308) of a first replicate (302) are displayed in a column for analysis by a user. The determination of a set of best beats is described in further detail below in, for example, the flowchart of FIG. 2. A second replicate (310) and third replicate (312) of the same time point may also be displayed adjacent to the first replicate (310). In this manner, a user may easily analyze an entire time point in one view to determine the highest quality beats to be measured for the time point. This is particularly advantageous over prior user interfaces that display only one to three beats on graphical user interface (GUI) per time point.

Once a network interface (110) receives ECG signal data generated by an ECG (104), the controller (112) of the processing device (108) may be configured to determine an ECG signal quality score and generate indexing information for a ranked or ordered set of consecutive cardiac beats (e.g., set of multi-beat sequences). The ranked set of MBS may be determined as described in further detail below. An ECG signal quality score may be determined based on the ranked set of beats. The QT evaluation may be for one or more of a TQT study, First-in-man, Phase I study, Phase II study, and Phase III study. Further processing performed by controller is described in more detail below with respect to FIG. 2. In some variations. The controller (112) and processing performed thereon may be disposed in ECG device (104).

A. Controller

A processing device (108), as depicted in FIG. 1, may comprise a controller (112) in communication with one or more ECG devices (104). The controller (112) may comprise one or more processors and one or more machine-readable memories in communication with the one or more processors. The processor may incorporate data received from memory and operator input to control the processing device (108). The inputs to the controller (112) may be received from one or more machine generated (e.g., ECG devices) and/or human generated sources (e.g., user input). The memory may further store instructions to cause the processor to execute modules, processes and/or functions associated with the processing device, such as the method steps described herein. The controller (112) may be connected to the one or more ECG devices (104) by wired or wireless communication channels. The controller (112) may be configured to control one or more components of the processing device (108) including the network interface (110) and user interface (116).

The controller (112) may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks. Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like, and portable or wearable augmented reality devices that interface with an operator's environment through sensors and may use head-mounted displays for visualization, eye gaze tracking, and user input.

i. Processor

The processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), and the like. The processor may be configured to run and/or execute application processes and/or other modules, processes and/ or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., siliconconjugated polymer and metal-conjugated polymer-metal structures), mixed analog and digital, and the like.

In some variations, one or more processors may execute the methods described herein in a cloud computing environment or as a Software as a Service (SaaS). For example, at least some of the steps of the methods described herein may be performed by a group of computers in communication via a network (e.g., the Internet) and via one or more appropriate interfaces (e.g., APIs). The cloud computing system may include clients and servers. A client and server are generally remote from each other and typically interact through a communication network. The relationship of client and server arises by virtue of computer programs running on the respective computers and having a client-server relationship to each other.

ii. Memory

In some variations, the memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, and the like. As used herein, database refers to a data storage resource. The memory may store instructions to cause the processor to execute modules, processes and/or functions associated with the processing device (108), such as ECG signal data processing, communication, display, and/or user settings. In some variations, storage may be network-based and accessible for one or more authorized users. Network-based storage may be referred to as remote data storage or cloud data storage. ECG signal data stored in cloud data storage (e.g., database (120)) may be accessible to respective users via a network, such as the Internet. In some variations, database (120) may be a cloud-based FPGA.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for a specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs); holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

B. User Interface

A user interface (116) may permit an operator to interact with and/or control the processing device (108) directly and/or remotely. For example, the user interface (116) may include an input device for an operator to input commands and an output device for an operator and/or other observers to receive output (e.g., view patient data on a display device) related to operation of the processing device (108).

User interface (116) may serve as a communication interface between an operator and the processing device (108). In some variations, the user interface (116) may comprise an input device and output device (e.g., touch screen and display) and be configured to receive input data and output data from one or more of the ECG device (104), computing devices (106, 118, 120, 122), input device, and output device. For example, ECG signal data generated by ECG device (104) may be processed by controller (112) and displayed by the output device (e.g., monitor display). As another example, operator control of an input device (e.g., joystick, keyboard, touch screen) may be received by user interface (116) and then processed by controller (112) for user interface (116) to output a control signal to one or more of the processing device (108) and ECG device (104).

i. Output Device

An output device of a user interface (116) may output ECG signal data corresponding to a subject (102), and may comprise one or more of a display device and audio device. The display device may be configured to display a graphical user interface (GUI). A display device may permit an operator to view ECG signal data and/or other data processed by the controller (112). In some variations, an output device may comprise a display device including one or more of a light emitting diode (LED), liquid crystal display (LCD), electroluminescent display (ELD), plasma display panel (PDP), thin film transistor (TFT), organic light emitting diodes (OLED), electronic paper/e-ink display, laser display, and holographic display.

An audio device may audibly output subject data, sensor data, system data, alarms and/or warnings. In some variations, an audio device may comprise at least one of a speaker, piezoelectric audio device, magnetostrictive speaker, and/or digital speaker. In some variations, an operator may communicate with other users using the audio device and a communication channel. For example, the operator may form an audio communication channel (e.g., VoIP call) with a remote operator, ECG technician, and/or subject.

ii. Input Device

Some variations of an input device may comprise at least one switch configured to generate a control signal. For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, pointing device (e.g., mouse), trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio and recognize an operator voice as a control signal.

B. Network Interface

As depicted in FIG. 1, a processing device (108) described herein may communicate with one or more networks (105) and computing devices (118, 120, 122) through a network interface (110). In some variations, the processing device (108) may be in communication with other devices via one or more wired and/or wireless networks. For example, the network interface (110) may permit the processing device (108) to communicate with one or more of a network (105) (e.g., Internet), remote server (122), and database (120). The network interface (110) may facilitate communication with other devices over one or more external ports (e.g., Universal Serial Bus (USB), multi-pin connector) configured to couple directly to other devices or indirectly over a network (e.g., the Internet, wireless LAN).

In some variations, the network interface (110) may comprise radiofrequency (RF) circuitry (e.g., RF transceiver) including one or more of a receiver, transmitter, and/or optical (e.g., infrared) receiver and transmitter configured to communicate with one or more devices and/or networks. RF circuitry may receive and transmit RF signals (e.g., electromagnetic signals). The RF circuitry converts electrical signals to/from electromagnetic signals and communicates with communications networks and other communications devices via the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like. A wireless network may refer to any type of digital network that is not connected by cables of any kind. Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet Message Access Protocol (IMAP) and/or Post Office Protocol (POP)), instant messaging (e.g., eXtensible Messaging and Presence Protocol (XMPP), Session Initiation Protocol for Instant Messaging and Presence Leveraging Extensions (SIMPLE), and/or Instant Messaging and Presence Service (IMPS)), and/or Short Message Service (SMS), or any other suitable communication protocol. Some wireless network deployments combine networks from multiple cellular networks or use a mix of cellular, Wi-Fi, and satellite communication. In some variations, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). As used herein, network refers to any combination of wireless, wired, public, and private data networks that are typically interconnected through the Internet, to provide a unified networking and information access system.

II. Methods

Methods for characterizing an ECG signal are also described here. Generally, methods described here comprise receiving an ECG signal generated by an ECG device and generating index information of a ranked order of multi-beat sequences derived from the ECG signal. The index information may correspond to a stability metric for the set of multi-beat sequences. A segment of a ECG recording, such as an epoch, may be analyzed. For example, each sequence of a predetermined number of consecutive cardiac beats (e.g., a multi-beat sequence of three consecutive cardiac beats) may form a set of multi-beat sequences for analysis and ranking or ordering. The multi-beat sequences may be sequential and/or include overlapping beats.

The methods described herein may provide improved precision and accuracy in QTc measurement, as well as in other common ECG-based measurements (e.g. QRS and PR), by selection of one or more multi-beat sequences having minimal variability with respect to a set of ECG parameters, thus enabling a reduction of the sample size or in the risk of false positive or other incorrect results relative to cardiac safety assessment in drug development. For instance, improved precision and accuracy may be utilized in late phase trials to avoid a subject being inadvertently excluded from studies due to QT/QTc interval prolongation that incorrectly indicates that the subject is above an exclusion threshold, or to minimize incorrect assessments about the effect of a drug being tested on ECG-based intervals.

For example, the internal algorithms and processing used in conventional ECG devices may determine that a patient's QTc interval derived from a subject's ECG signal as greater than 450 milliseconds, which typically excludes the patient from further participation in a clinical trial. However, the same ECG signal processed using the devices as described herein may generate a QTc interval below the 450 millisecond exclusion threshold, thus enabling that subject to continue participating in the clinical trial instead of being excluded. In another key application of this invention, conventional ECG devices or conventional methods of measuring ECGs may determine that safety ECGs obtained from a Phase II or III trial indicate that an individual effect (e.g., an adverse event) or a group effect (e.g., an effect on a population) has occurred as a result of the tested drug. However, the same ECG signal processed in the manner described herein may result in more accurate information indicating no such effect or a different effect, enabling a more accurate assessment and understanding of the study drug's true effect.

In some variations, the methods may analyze large volumes of ECG data to generate a cardiac safety profile from a standard Phase I study. The techniques disclosed herein may be applied to patient population studies as well as healthy normal studies, although more patients are likely needed in patient population studies as compared to healthy volunteer studies. In some variations, the methods may analyze data from Phase II and III trials to more optimally assess whether a studied drug is causing adverse or potentially dangerous effects on particular study subjects, or to more accurately assess which subjects should be included, excluded and/or discontinued from a trial based on certain ECG-based parameters.

Figure 2:
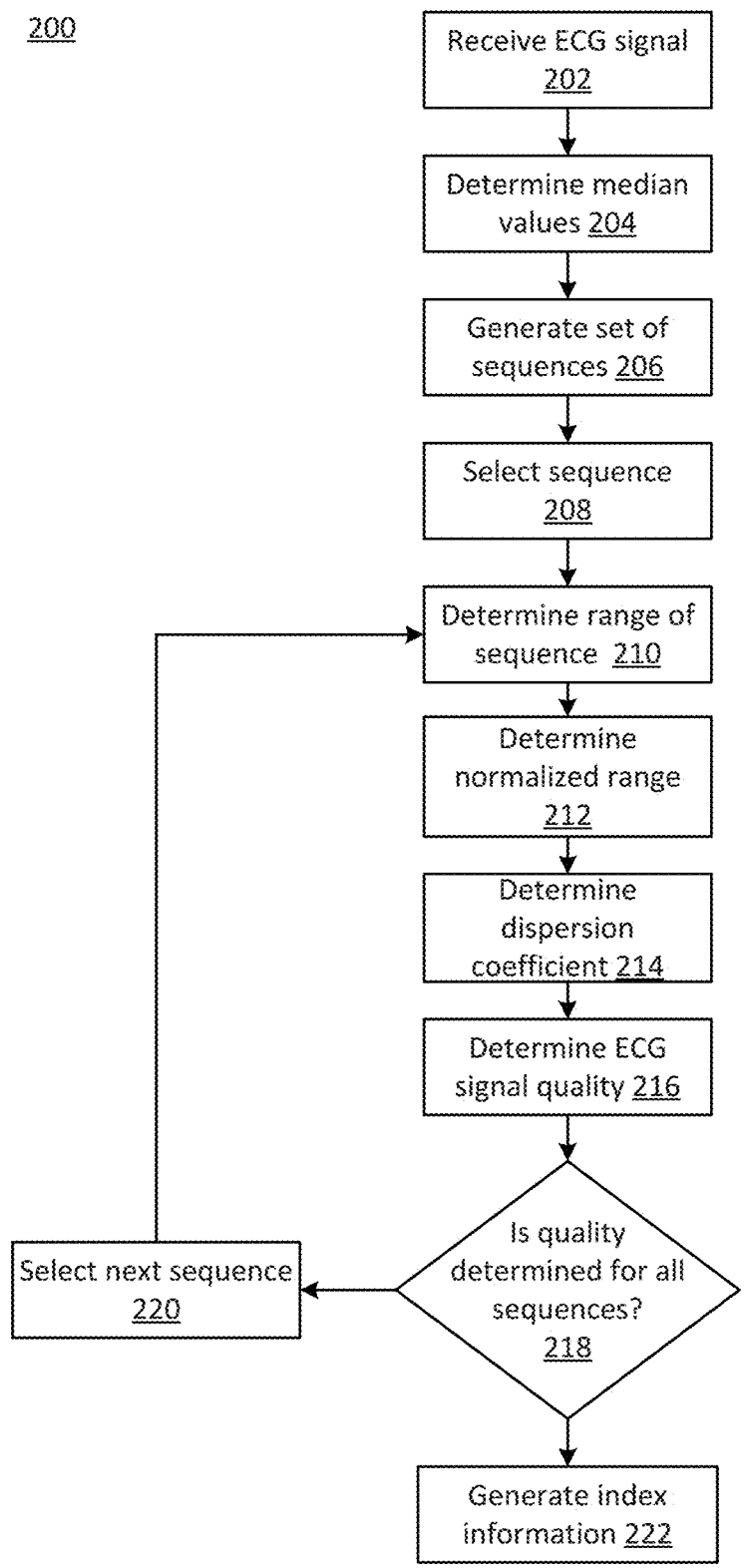
FIG. 2 depicts one variation of a flowchart of an ECG signal quality determination process.
Figure 3:
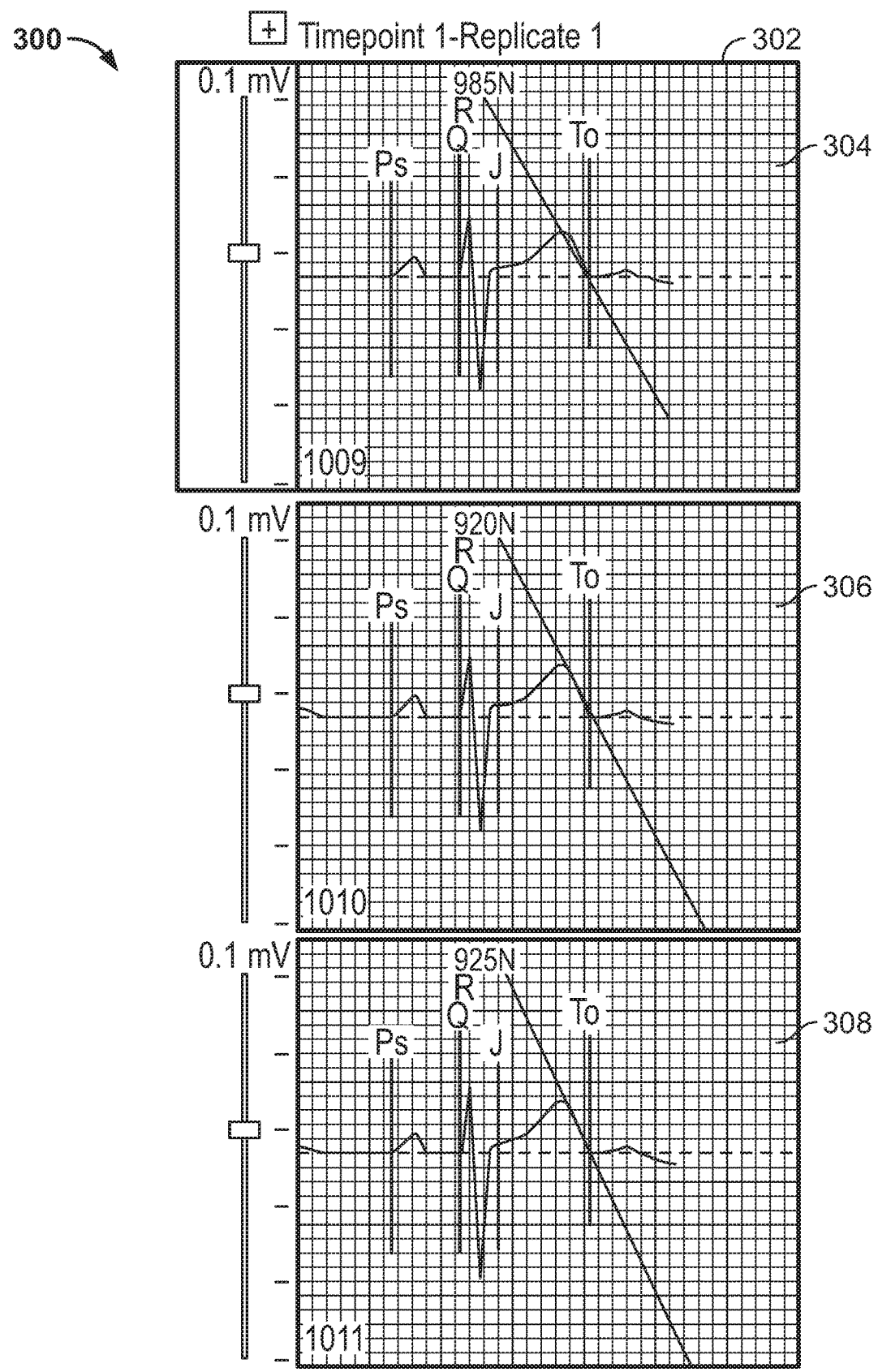
FIG. 3 depicts one variation of a graphical user interface of an ECG processing system.
Figure 3:
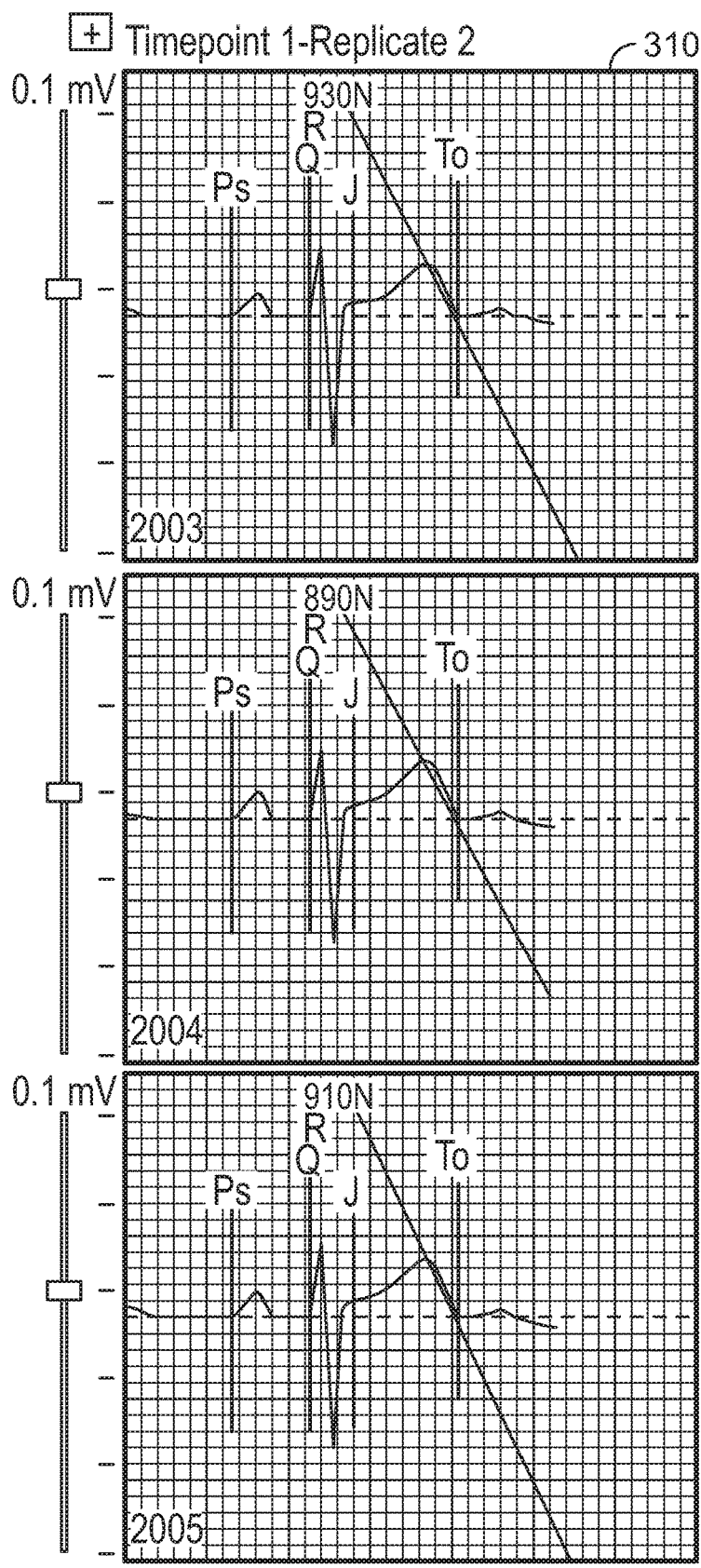
Figure 3:
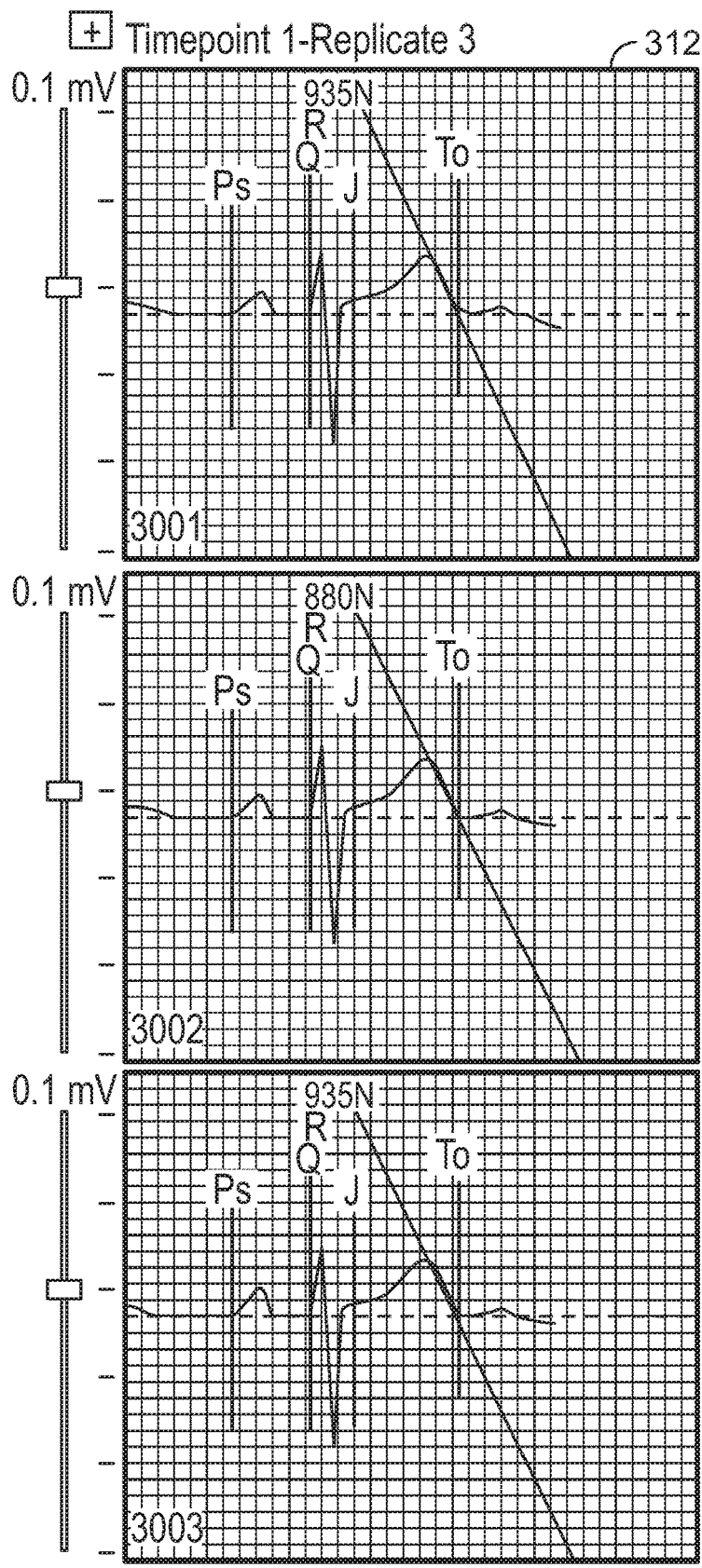

FIG. 2 depicts one variation of a flowchart to characterize an ECG signal (200). For the sake of example, the ECG signal analysis described with respect to FIG. 2 is based on the ECG parameters of QT, PR, and QRS. In some variations, the ECG signal data may be received in parallel and/or serially from a plurality of ECG devices, patients, data formats, clinical site locations and studies. The process (200) may begin with connecting an ECG device to a subject. The ECG signal(s) generated by an ECG device coupled to a subject (202) may be received by a processing device. In some of these variations, median values of an epoch (having a plurality of consecutive cardiac beats) of the ECG signal may optionally be determined (204). A set of multi-beat sequences (e.g., 3 consecutive cardiac beats) may be generated for the plurality of consecutive cardiac beats of the ECG signal (206). For example, the set of multi-beat sequences may include every sequence of 3 consecutive cardiac beats of an epoch of the ECG signal. The ECG epoch may comprise at least one replicate having a length of about ten seconds, for example. The ECG signal quality may be determined for each MBS. A first multi-beat sequence of the set of multi-beat sequences may be selected for processing (208). A range of the measurement values may be determined for each of the plurality of ECG parameters (210). Range $R_{ep}(x)$ may be determined as follows:

$R_{ep}(QT) = \text{Max}(QT_n) - \text{Min}(QT_n)$ where $QT_n$ are the $n=3$ measurements of the $QT$ interval for each of the multi-beat sequences.

$R_{ep}(PR) = \text{Max}(PR_n) - \text{Min}(PR_n)$ where $PR_n$ are the $n=3$ measurements of the $PR$ interval for each of the multi-beat sequences.

$R_{ep}(QRS) = \text{Max}(QRS_n) - \text{Min}(QRS_n)$ where $QRS_n$ are the $n=3$ measurements of the $QRS$ interval for each of the multi-beat sequences.

A normalized range of the measurements may be determined for the MBS for each of the plurality of ECG parameters (212) using the determined range in step 210. Normalized range $\widetilde{Rep}(x)$ may be determined as follows:

$$\widetilde{Rep}(QT) = \frac{Rep(QT)}{\overline{QT}} \text{ where } \overline{QT} \text{ is the average } QT \text{ values within the epoch.}$$

$$\widetilde{Rep}(PR) = \frac{Rep(PR)}{\overline{PR}} \text{ where } \overline{PR} \text{ is the average } PR \text{ values within the epoch.}$$

$$\widetilde{Rep}(QRS) = \frac{Rep(QRS)}{\overline{QRS}} \text{ where } \overline{QRS} \text{ is the average } QRS \text{ values within the epoch.}$$

A dispersion coefficient may be determined (214) based on the determined range (210) and determined normalized range (212). The dispersion coefficient may be an evenly weighted sum of the normalized range of the plurality of ECG parameters. The dispersion coefficient DP may be determined as follows:

$$DP = (C1)\widetilde{Rep}(QT) + (C2)\widetilde{Rep}(PR) + (C3)\widetilde{Rep}(QRS) \text{ where } C1=C2=C3=0.33$$

In some variations, the dispersion coefficient DP may be weighted evenly between QT, PR and QRS. However, the weight for each interval may me be modified. For example, dispersion coefficient DP may be independent from QT by setting C1=0.

The ECG signal quality for the selected multi-beat sequence may be determined (216). The ECG signal quality may be based on the dispersion coefficient and a deviation from average of each of a plurality of ECG parameters. The deviation from average may comprise a sum of differences between the multi-beat sequence and an average from the epoch for each of the plurality of ECG parameters. The ECG signal quality Q may be determined as follows:

$$Q = DP * (\overline{\overline{PR}} + \overline{\overline{QRS}} + \overline{\overline{QT}}) \text{ where}$$

$\overline{\overline{PR}}$ is the deviation of current PR interval to the average PR ($\overline{PR}$) within the epoch;

$\overline{\overline{QRS}}$ is the deviation of current QRS interval to the average QRS ($\overline{QRS}$) within the epoch; and $\overline{\overline{QT}}$ is the deviation of current QT interval to the average QT ($\overline{QT}$) within the epoch.

A determination is made whether an ECG signal quality score Q has been determined for each multi-beat sequence in the set of multi-beat sequence (218). A number of ECG signal quality values of an epoch may equal a number of cardiac beats minus two if all the cardiac beats are sinus. If not, then a next multi-beat sequence is selected (220) and processed through steps 210-216. Once all MBS are processed (218), index information may be generated for the set of multi-beat sequences of the epoch. The set of multi-beat sequences MBS may be ordered (222) based upon the ECG signal quality Q. In some variations, the set of MBS may be provided in ascending order for each MBS based on the determined ECG signal quality Q. A subset of the ordered multi-beat sequences (e.g., or one or more ordered/ranked/classified groups) may then be selected for further evaluation (e.g., QT, QRS, PR evaluation) associated with a new chemical entity using the index information. The QT evaluation may be for one or more of a TQT study, First-in-man, Phase I study, Phase II study, and Phase III study. In some variations, subject participation in one or more studies may be determined using the index information. For example, subject participation may include exclusion of a subject from one or more studies when the QT evaluation comprises a QTc in excess of 450 milliseconds. In some variations, the subject may be disconnected from the ECG device upon determining the ECG signal quality such that processing of ECG signal data may be performed in real-time with the subject's ECG recording. In some variations, a second ECG signal may be received from the ECG device coupled to the subject if the ECG signal quality of the plurality of consecutive cardiac beats exceeds a predetermined threshold corresponding to one or more of the dispersion coefficient and the deviation from the average of each of the plurality of ECG parameters. In some variations, one or more segments of the ECG signal may be extracted using the indexing information to generate a reduced size ECG signal data set suitable for further evaluation.

Although the foregoing inventions have, for the purposes of clarity and understanding, been described in some detail by way of illustration and example, it will be apparent that certain changes and modifications may be practiced, and are intended to fall within the scope of the appended claims. Additionally, it should be appreciated that the devices described here may comprise any combination of device components and features described above.

We claim:

1. A method comprising:
   receiving an ECG signal generated by an ECG device coupled to a subject, the ECG signal comprising a plurality of consecutive cardiac beats;
   determining ECG signal quality of the plurality of consecutive cardiac beats based on a dispersion coefficient and a deviation from an average of each of a plurality of ECG parameters; and
   generating indexing information for a set of sequences from the plurality of consecutive cardiac beats, wherein each sequence of the set of sequences comprises a first predetermined number of consecutive cardiac beats, wherein the set of sequences are ordered based upon the ECG signal quality; and
   determining subject participation in a study using the indexing information, wherein the subject participation comprises exclusion from the study when a QT evaluation comprises a QTc in excess of 450 milliseconds.

2. The method of claim 1, wherein the ECG signal comprises an epoch comprising a second predetermined number of consecutive cardiac beats.

3. The method of claim 2, wherein the ECG signal quality is determined for each sequence of the set of sequences.

4. The method of claim 3, wherein the deviation from the average of each of the plurality of ECG parameters comprises a sum of differences for a sequence and its average from the epoch for each of the plurality of ECG parameters.

5. The method of claim 4, wherein the ECG signal quality is $Q=DP*(\Sigma \tilde{x})$, where DP is the dispersion coefficient and $\tilde{x}$ is a deviation between a sequence and an average of an epoch for an ECG parameter.

6. The method of claim 5, wherein the dispersion coefficient is based on a range and a normalized range for each of the plurality of ECG parameters.

7. The method of claim 6, wherein the dispersion coefficient is an evenly weighted sum of the normalized range of the plurality of ECG parameters.

8. The method of claim 6, wherein the range is $Rep(x) = Max(x) - Min(x)$, where x comprises one of the ECG parameters.

9. The method of claim 8, wherein the normalized range is $$\widetilde{Rep}(x) = \frac{Rep(x)}{\bar{x}},$$

where $\bar{x}$ is an average value of one of the ECG parameters within the epoch.

10. The method of claim 1, wherein the ECG parameters comprise QT, PR, and QRS.

11. The method of claim 2, wherein the first predetermined number is two or more, and the second predetermined number is greater than the first predetermined number.

12. The method of claim 3, further comprising ordering the set of sequences in ascending order based on the ECG signal quality.

13. The method of claim 12, further comprising selecting a subset of the set of sequences ordered in ascending order based on the ECG signal quality for the QT evaluation using the indexing information, wherein the QT evaluation is associated with a new chemical entity.

14. The method of claim 13, wherein the QT evaluation comprises one or more of a Thorough QT (TQT) study, phase I study, phase II study, and phase III study.

15. The method of claim 12, further comprising selecting a subset of the set of sequences ordered in ascending order based on the ECG signal quality for one or more of QRS and PR evaluation associated with a new chemical entity using the indexing information.

16. The method of claim 1, further comprising:
connecting the ECG device to the subject; and
disconnecting the ECG device from the subject;
wherein determining ECG signal quality of the plurality of consecutive cardiac beats is performed prior to disconnecting the ECG device from the subject.

17. The method of claim 16, further comprising receiving a second ECG signal from the ECG device coupled to the subject if the ECG signal quality of the plurality of consecutive cardiac beats exceeds a predetermined threshold corresponding to one or more of the dispersion coefficient and the deviation from the average of each of the plurality of ECG parameters.

18. The method of claim 1, further comprising extracting one or more segments of the ECG signal using the indexing information.

* * * * *